(12) United States Patent
Duijsens et al.

(10) Patent No.: US 11,819,686 B2
(45) Date of Patent: Nov. 21, 2023

(54) MEDICAL DEVICE ANCHORING

(71) Applicant: Medtronic, Inc., Minneapolis, MN (US)

(72) Inventors: Victor Duijsens, Grevenbicht (NL); Carmen Dimovski, Elk River, MN (US); Paul S. Kratoski, Brooklyn Park, MN (US); Joseph P. Ricci, Ham Lake, MN (US); Paulus C. van Venrooij, Hoensbroeck (NL)

(73) Assignee: Medtronic, Inc., Minneapolis, MN (US)

( * ) Notice: Subject to any disclaimer, the term of this patent is extended or adjusted under 35 U.S.C. 154(b) by 291 days.

(21) Appl. No.: 16/840,849

(22) Filed: Apr. 6, 2020

(65) Prior Publication Data
US 2020/0230398 A1 Jul. 23, 2020

Related U.S. Application Data

(63) Continuation of application No. 15/689,357, filed on Aug. 29, 2017, now Pat. No. 10,610,681.

(51) Int. Cl.
*A61N 1/05* (2006.01)
*A61M 25/04* (2006.01)
(Continued)

(52) U.S. Cl.
CPC ............ *A61N 1/0539* (2013.01); *A61B 90/11* (2016.02); *A61M 25/04* (2013.01);
(Continued)

(58) Field of Classification Search
CPC .. A61N 1/0539; A61N 1/0452; A61N 1/0456; A61B 90/10; A61B 90/11;
(Continued)

(56) References Cited

U.S. PATENT DOCUMENTS 5,464,446 A 11/1995 Dreesen et al.
5,693,032 A 12/1997 Bierman ............... A61M 25/02
604/174
(Continued)

FOREIGN PATENT DOCUMENTS

EP 1016432 7/2000
GB 2344054 5/2000

OTHER PUBLICATIONS

U.S. Appl. No. 62/400,140, filed Sep. 27, 2016.
U.S. Appl. No. 62/446,923, filed Jan. 17, 2017.

*Primary Examiner* — Tuan V Nguyen
(74) *Attorney, Agent, or Firm* — Mueting Raasch Group

(57) ABSTRACT

An apparatus for fastening around a cranial burr hole includes a substantially flat core and a shell encapsulating a ring portion of the core. The shell defines an orifice substantially centered within the ring portion, and has a contoured lower surface to match the cranial curvature. Pliable arms of the core extend laterally from the ring portion, each being terminated by a fastener member. A central portion of a placement tool for the apparatus has a lower part configured to extend through the apparatus orifice, and an upper part from which first and second arms of the tool extend laterally. Each tool arm is terminated with a receptacle to hold a bone screw, and, when the tool central portion lower part extends through the apparatus orifice, each receptacle aligns with a corresponding fastener member, and lower openings of the receptacles are generally oriented along the contoured lower surface.

20 Claims, 7 Drawing Sheets

(51) Int. Cl.
  *A61B 90/11*   (2016.01)
  *A61M 25/02*   (2006.01)
  *A61B 17/34*   (2006.01)
  *A61N 1/36*    (2006.01)
  *A61B 90/10*   (2016.01)

(52) U.S. Cl.
  CPC ... *A61B 17/3468* (2013.01); *A61B 2017/3407* (2013.01); *A61B 2090/103* (2016.02); *A61M 2025/024* (2013.01); *A61M 2025/028* (2013.01); *A61M 2025/0213* (2013.01); *A61M 2025/0286* (2013.01); *A61N 1/0534* (2013.01); *A61N 1/36014* (2013.01); *A61N 1/36067* (2013.01)

(58) Field of Classification Search
  CPC .............. A61B 90/39; A61B 2090/101; A61B 2090/103; A61B 5/064; A61B 5/055; A61B 5/062; A61M 25/04
  See application file for complete search history.

(56) References Cited

U.S. PATENT DOCUMENTS

| | | |
|---|---|---|
| 5,843,150 A | 12/1998 | Dreesen et al. |
| 5,865,842 A | 2/1999 | Knuth et al. |
| 5,927,277 A | 7/1999 | Baudino et al. |
| 5,954,687 A | 9/1999 | Baudino |
| 6,044,304 A | 3/2000 | Baudino |
| 6,134,477 A | 10/2000 | Knuteson |
| 6,210,417 B1 | 4/2001 | Baudino et al. |
| 6,214,016 B1 | 4/2001 | Williams et al. |
| 6,267,769 B1 | 7/2001 | Truwit |
| 6,321,104 B1 | 11/2001 | Gielen et al. |
| 6,752,812 B1 | 6/2004 | Truwit |
| 6,902,569 B2 | 6/2005 | Parmer et al. |
| 7,033,326 B1 | 4/2006 | Pianca et al. |
| 7,177,701 B1 | 2/2007 | Pianca |
| 7,204,840 B2 | 4/2007 | Skakoon et al. |
| 7,235,084 B2 | 6/2007 | Skakoon et al. |
| 7,346,391 B1 | 3/2008 | Osorio et al. |
| 7,421,297 B2 | 9/2008 | Giftakis et al. |
| 7,580,756 B2 | 8/2009 | Schulte et al. |
| 7,588,581 B2 | 9/2009 | Solar et al. |
| 7,604,644 B2 | 10/2009 | Schulte et al. |
| 7,604,655 B2 | 10/2009 | Warnick |
| 7,637,915 B2 | 12/2009 | Parmer et al. |
| 7,704,260 B2 | 4/2010 | Skakoon et al. |
| 7,749,199 B2 | 7/2010 | Mogg |
| 7,766,394 B2 | 8/2010 | Sage et al. |
| 7,949,410 B2 | 5/2011 | Rodriguez |
| 7,981,119 B2 | 7/2011 | Lando et al. |
| 7,981,120 B2 | 7/2011 | Mazzocchi et al. |
| 8,007,473 B2 | 8/2011 | Smith et al. |
| 8,038,685 B2 | 10/2011 | Bedenbaugh |
| 8,050,772 B1 | 11/2011 | Daglow et al. |
| 8,315,714 B2 | 11/2012 | Daglow et al. |
| 8,417,353 B2 | 4/2013 | Appenrodt et al. |
| 8,425,534 B2 | 4/2013 | Barker |
| 8,556,860 B2 | 10/2013 | Stratton ............... A61M 39/02 604/174 |
| 8,603,038 B2 | 12/2013 | Nelson |
| 8,731,686 B2 | 5/2014 | Lane et al. |
| 8,738,151 B2 | 5/2014 | Nelson |
| 8,945,089 B2 | 2/2015 | Johnson et al. |
| 9,468,751 B2 | 10/2016 | Bonde |
| 9,474,896 B2 | 10/2016 | Lopez |
| 9,539,421 B2 | 1/2017 | Bonde et al. |
| 9,604,052 B2 | 3/2017 | Behymer et al. |
| 2002/0052610 A1* | 5/2002 | Skakoon ............... A61B 34/20 606/129 |
| 2005/0075680 A1 | 4/2005 | Lowry ................. A61N 1/0531 607/45 |
| 2005/0182420 A1 | 8/2005 | Schulte et al. |
| 2005/0182421 A1 | 8/2005 | Schulte et al. |
| 2005/0182422 A1 | 8/2005 | Schulte et al. |
| 2005/0182423 A1 | 8/2005 | Schulte et al. |
| 2005/0182424 A1 | 8/2005 | Schulte et al. |
| 2005/0182425 A1 | 8/2005 | Schulte et al. |
| 2005/0182464 A1 | 8/2005 | Schulte et al. |
| 2005/0192594 A1 | 9/2005 | Skakoon et al. |
| 2007/0249980 A1 | 10/2007 | Carrez et al. |
| 2008/0017206 A1 | 1/2008 | Becker et al. |
| 2008/0172068 A1 | 7/2008 | Adams et al. |
| 2009/0112327 A1 | 4/2009 | Lane et al. |
| 2009/0118804 A1 | 5/2009 | Moffitt et al. |
| 2010/0268308 A1 | 10/2010 | Rossby ............. A61M 39/0247 607/116 |
| 2012/0209206 A1 | 8/2012 | Scandone, Jr. ........ A61M 25/04 604/175 |
| 2012/0316628 A1 | 12/2012 | Lopez ................. A61N 1/0539 607/116 |
| 2013/0018319 A1 | 1/2013 | Abe .................... A61M 25/02 604/174 |
| 2013/0066410 A1 | 3/2013 | Funderburk ......... A61N 1/0539 607/116 |
| 2013/0066430 A1* | 3/2013 | Funderburk .......... A61F 2/2875 623/17.19 |
| 2014/0257325 A1 | 9/2014 | Chavez et al. |
| 2015/0148747 A1 | 5/2015 | Whitley ............ A61M 39/1011 604/180 |
| 2016/0361529 A1 | 12/2016 | Finch, Jr. .......... A61M 39/0247 |

\* cited by examiner

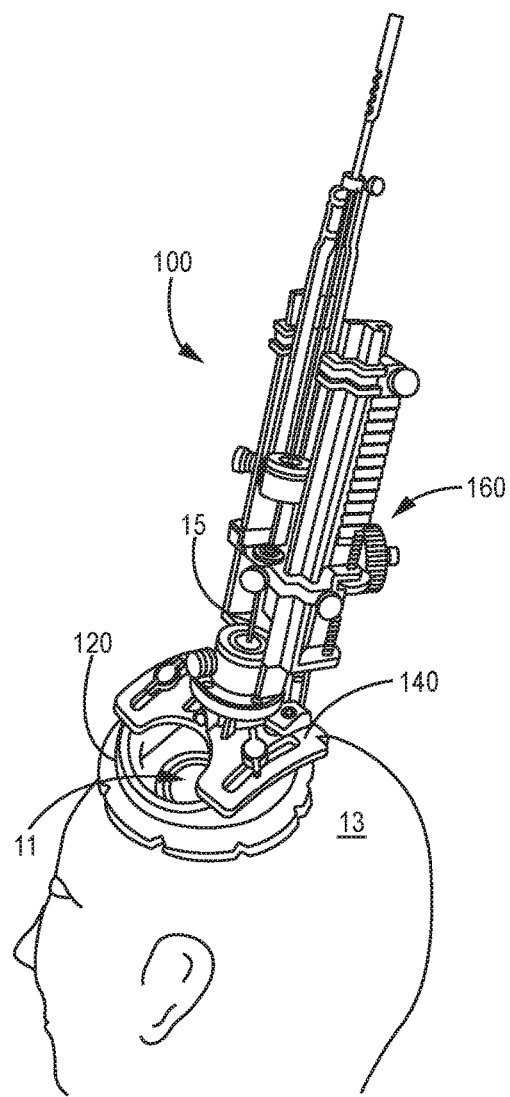
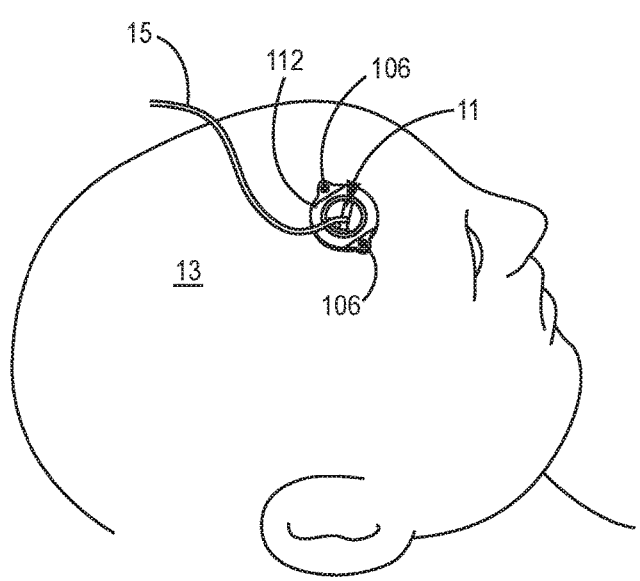
FIG. 1A  FIG. 1B

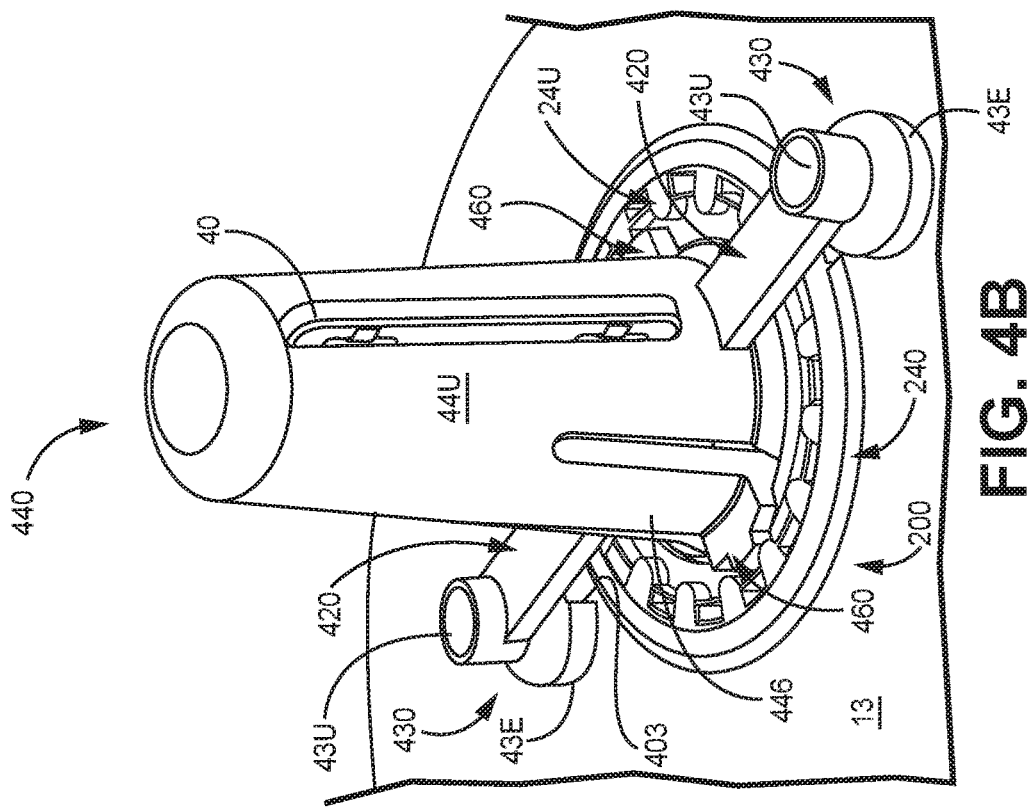
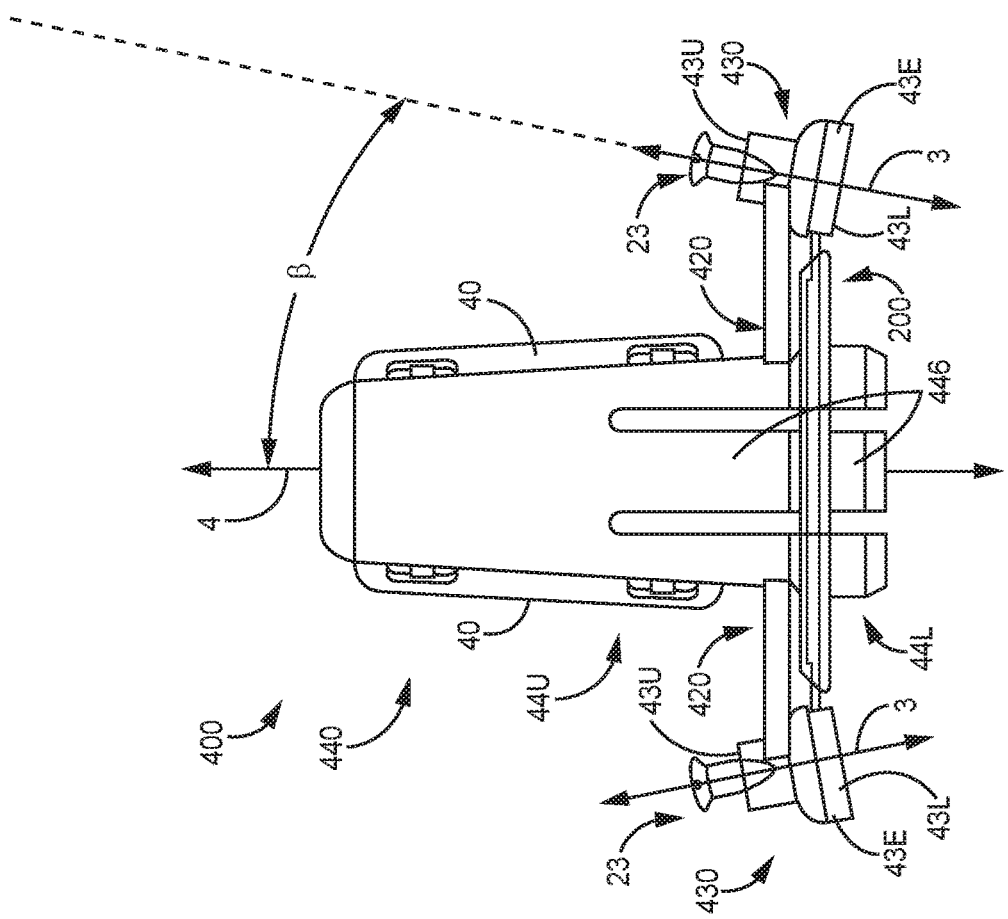
FIG. 4B
FIG. 4A

MEDICAL DEVICE ANCHORING

TECHNICAL FIELD

The present disclosure pertains to anchoring medical devices of implantable medical therapy systems, and more particularly to apparatus, tools, and systems that facilitate the anchoring of an elongate portion of the medical device within a body portal, for example, a burr hole formed in a patient's cranium.

BACKGROUND

Medical procedures for treating a variety of neurological conditions, for example, Parkinson's disease, essential tremor and dystonia, require access to the brain, typically through a burr hole formed in the cranium, for the insertion of deep brain stimulating electrodes. Burr holes may also be formed for the insertion of a delivery catheter, for example, to provide drug therapy for similar conditions, or an extraction catheter, for example, a hydrocephalus shunt. Stereotactic apparatus and procedures, which are known to those skilled in the art, may be employed by surgeons to locate inserted electrodes and/or drug delivery ports in target regions of the brain.

FIG. 1A is a schematic showing an exemplary stereotactic guidance system 100 (e.g. Medtronic Nexdrive Micropositioning Drive attached to the Medtronic Nexframe®) mounted to a patient's cranium 13. FIG. 1A illustrates a ring 120 of guidance system 100, which extends around a perimeter of a body portal, or burr hole 11 formed in cranium 13, supporting a socket assembly 140 to which a micropositioning drive 160 is attached. An anchoring mechanism 112 (FIG. 1B; e.g. the Medtronic StimLoc®) may be mounted around burr hole 11 and fastened to cranium 13, for example, via bone screws received through holes 106 of a base ring of mechanism 112, prior to attaching ring 120 of guidance system 100. FIG. 1A further illustrates an elongate therapy delivery lead or catheter 15 of a medical device being held within drive 160 for advancement through burr hole 11 and into the cranial space for positioning on a target region of the brain.

FIG. 1B illustrates elongate therapy delivery lead or catheter 15 of the device extending through anchoring mechanism 112, after guidance system 100 has been removed. FIG. 1B further illustrates therapy delivery lead or catheter 15 extending through a slot of mechanism 112 to be anchored between mechanism 112 and a cap that snaps into place thereover (not shown; e.g., the Medtronic StimLoc® cap). Those skilled in the art appreciate that a proximal length of therapy delivery lead or catheter 15, outside the cranial space, may be routed, beneath the scalp and subcutaneously, to a therapy generator of the device, for example, a generator 28 that is shown, in the schematic of FIG. 1C, implanted subcutaneously in proximity to the patient's clavicle. With further reference to FIG. 1C, a distal length 154 of therapy delivery lead or catheter 15, which has been advanced through burr hole 11, is shown including therapy delivery ports, or electrodes 26A, 26B positioned at the target region.

BRIEF SUMMARY

Apparatus disclosed herein facilitate stable and low profile anchoring of elongate portions of implanted medical devices that extend through cranial burr holes. A system may include such an apparatus and a placement tool, as described below. Furthermore, an implantable medical therapy system, according to some embodiments, includes a medical device, and an anchoring mechanism for the device, together with any of the apparatus embodiments disclosed herein; and, according to some additional embodiments, a kit may include such a medical therapy system and the placement tool for the apparatus thereof.

Embodiments of the apparatus, which is configured to be fastened to a cranium, around a burr hole formed therethrough, and to receive attachment thereto a medical device anchoring mechanism, include a substantially flat core, for example, formed from a medical grade titanium, and a shell encapsulating a ring portion of the core, for example, formed from a medical grade polymer, wherein the shell defines an orifice substantially centered within the ring portion of the core, and a lower surface of the shell has a contour to match the curvature of cranium around the burr hole. The core further includes first and second pliable arms extending laterally from the ring portion, wherein each arm is terminated by a corresponding fastener member that has an aperture to receive extension of a bone screw therethrough. According to some embodiments, each fastener member has a concave surface that faces in a same direction as the lower surface of the shell, such that the aperture of each fastener member extends through an apex of the corresponding concave surface. A placement tool for the apparatus, according to some embodiments, includes a central portion that has a lower part configured to extend through the orifice of the apparatus, and an upper part from which first and second arms of the tool extend laterally. Each arm of the tool is terminated with a receptacle that is configured to hold a bone screw, and each receptacle extends from an upper opening to a lower opening thereof. When the lower part of the central portion of the tool extends through the orifice of the apparatus, each receptacle of the tool aligns with a corresponding fastener member of the apparatus, and the lower openings of the tool receptacles are generally oriented along the curvature of the contour of the apparatus lower surface.

BRIEF DESCRIPTION OF THE DRAWINGS

The following drawings are illustrative of particular embodiments and do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 1A is a schematic showing an exemplary stereotactic guidance system mounted to a patient's cranium;

FIG. 1B is a schematic showing an elongate therapy delivery lead or catheter of an implantable medical device extending through an anchoring mechanism after the guidance system has been removed;

FIG. 4A is an elevation view of a placement tool assembled together with the apparatus, according to some system embodiments; and FIGS. 4B-C are a perspective view and a cross-section view of the tool fitted in a cranial burr hole to place the apparatus thereabout for fastening to the cranium.

DETAILED DESCRIPTION

The following detailed description is exemplary in nature and is not intended to limit the scope, applicability, or configuration of inventive embodiments disclosed herein in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1C:
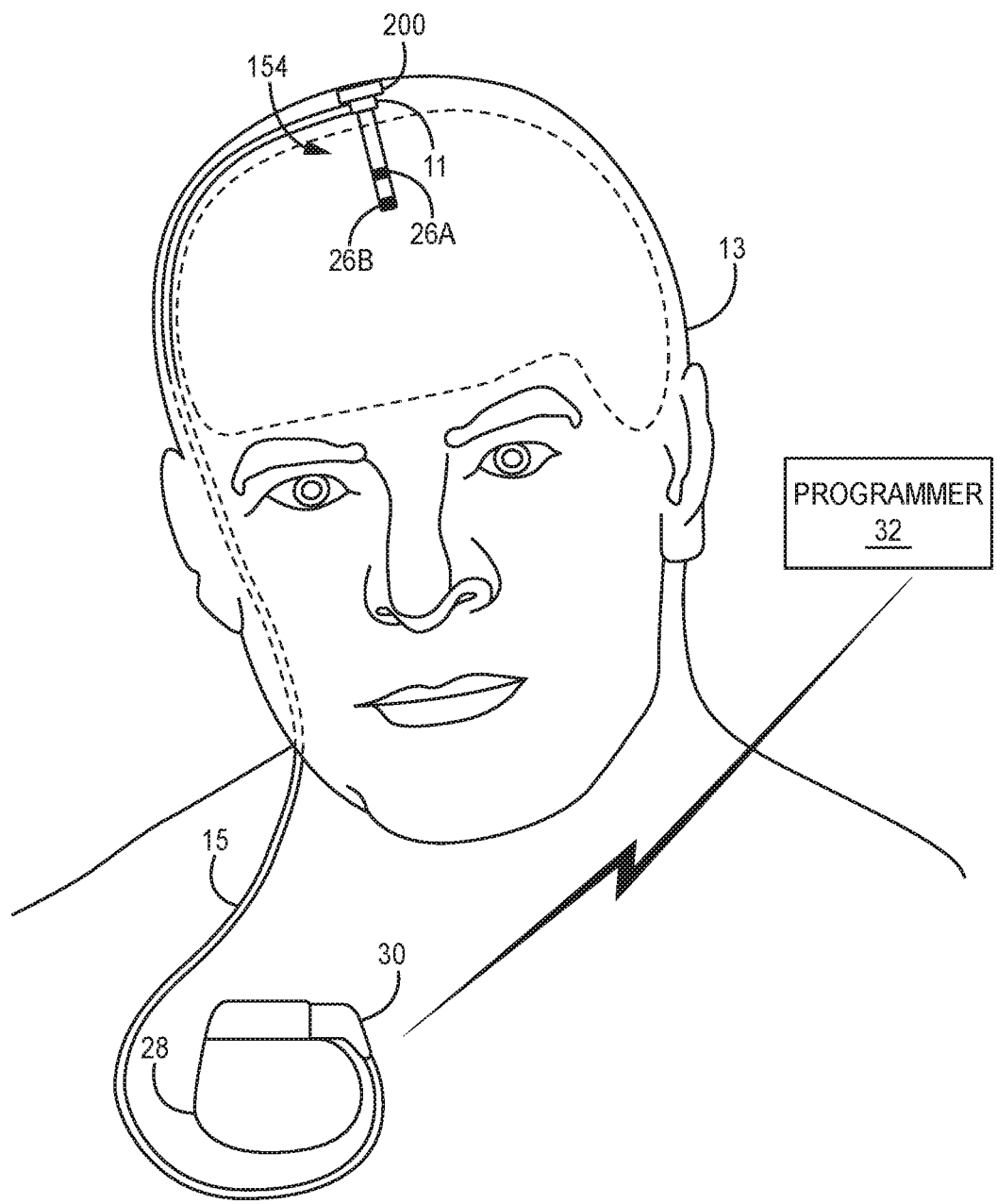
FIG. 1C is a schematic showing an implanted medical therapy system in which embodiments of the disclosure may be employed.

FIG. 1C is a schematic showing an implanted medical therapy system in which an apparatus 200 may be employed, according to some embodiments of the present disclosure. FIG. 1C illustrates the system including the aforementioned therapy generator 28 and elongate therapy delivery lead 15, also referred to herein generally as a therapy delivery device, which is shown coupled thereto via a connector 30 that terminates the proximal length thereof. In other examples, the therapy delivery device may be a catheter. According to an exemplary embodiment, therapy generator 28 is configured to deliver electrical stimulation therapy to, and/or sense electrical signals from the patient's brain, via lead electrodes 26A, 26B that are mounted to distal length 154 of lead 15 and electrically coupled to connector 30 via insulated conductors. Those skilled in the art are familiar with suitable configurations and constructions for lead 15 and generator 28. Therapy generator 28 may include processing circuitry, memory, signal generation circuitry, sensing circuitry, telemetry circuitry, and a power source, wherein the memory may include computer-readable instructions that are executed by the processing circuitry, for example, to deliver stimulation therapy to the patient, sense physiological signals of the patient, and/or perform other functions related to treating one or more conditions of the patient. The telemetry circuitry may include any suitable hardware, firmware, software or any combination thereof for communicating with another device, such as a programmer 32. Under the control of the processing circuitry the telemetry circuitry may receive downlink telemetry from and send uplink telemetry to programmer 32 with the aid of an antenna, which may be internal and/or external. Programmer 32 may be a handheld computing device, computer workstation, or networked computing device that includes electronics and other internal components necessary or desirable for executing the functions associated with the system.

FIG. 1C further illustrates lead distal length 154 extending through an apparatus 200, which is fastened to the patient's cranium 13 around the above-described burr hole 11. According to embodiments described below, apparatus 200 is configured to receive attachment thereto a medical device anchoring mechanism that secures lead 15 in place so that electrodes 26A, 26B remain positioned at the aforementioned target regions of the patient's brain for stimulation thereof over the course of the system implant.

Figure 2A:
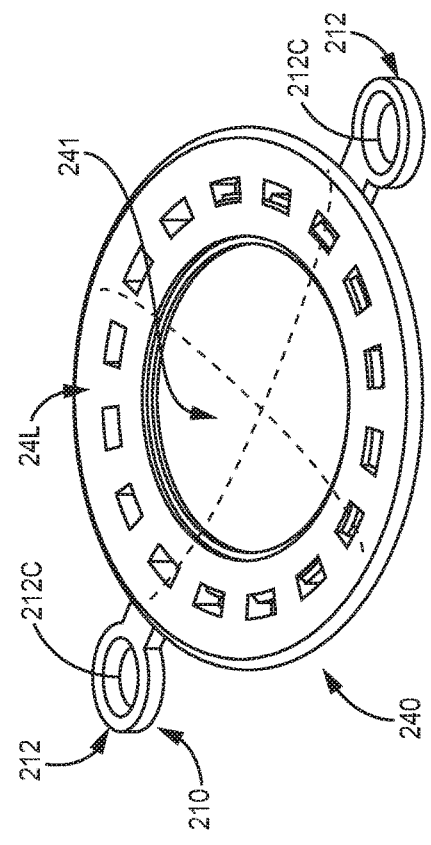
FIGS. 2A-B are perspective views of an apparatus, according to some embodiments.
Figure 2B:
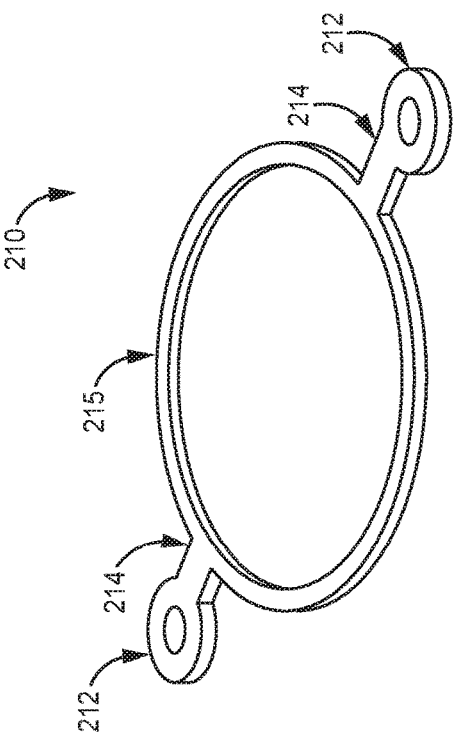
Figure 2C:
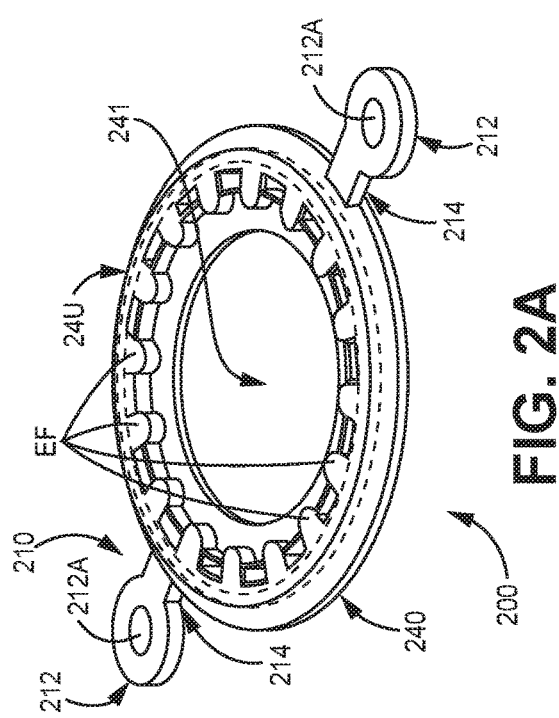
FIG. 2C is an elevation view of the apparatus, according to some embodiments.
Figure 2D:
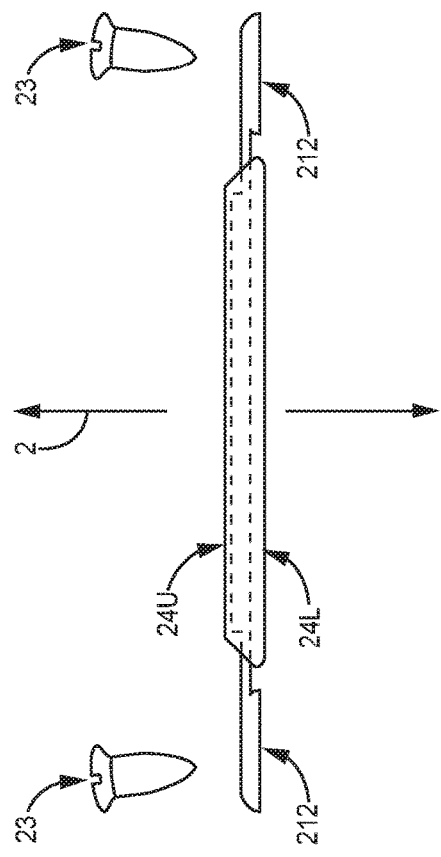
FIG. 2D is a perspective view of a core of the apparatus, according to some embodiments.

FIGS. 2A-B are perspective views of apparatus 200; and FIG. 2C is an elevation view of apparatus 200. FIGS. 2A-C illustrate apparatus 200 including a substantially flat core 210 and a shell 240, and FIG. 2D shows, in perspective view, core 210 without shell 240. FIG. 2D illustrates core 210 including a ring portion 215 and first and second pliable arms 214 extending laterally from ring portion 215, wherein each of first and second fastener members 212 of core 210 terminate a corresponding pliable arm 214. FIGS. 2A-C further illustrate shell 240 encapsulating ring portion 215. (Ring portion 215 is indicated with dashed lines in FIGS. 2A and 2C.) According to the illustrated embodiment, shell 240 defines an orifice 241 of apparatus 200, which is substantially centered within ring portion 215 of core 210. In FIG. 2B, dashed lines accentuate a curved contour of a lower surface 24L of shell 240, to match a curvature of the patient's cranium (e.g. cranium 13 of FIGS. 1A-C). But core 210, being substantially flat, extends within shell 240 without such a curvature. Core 210 is preferably formed from a medical grade titanium, for example, machined, and shell 240 from a medical grade polymer, such as polysulfone or polyether ether ketone (PEEK), for example, being insert molded around core 210. According to an exemplary embodiment, the curvature of shell lower surface 24L corresponds to an approximately ten inch diameter cranium, and a nominal maximum thickness between upper surface 24U and lower surface 24L may be approximately 0.05 inch.

Figure 2E:
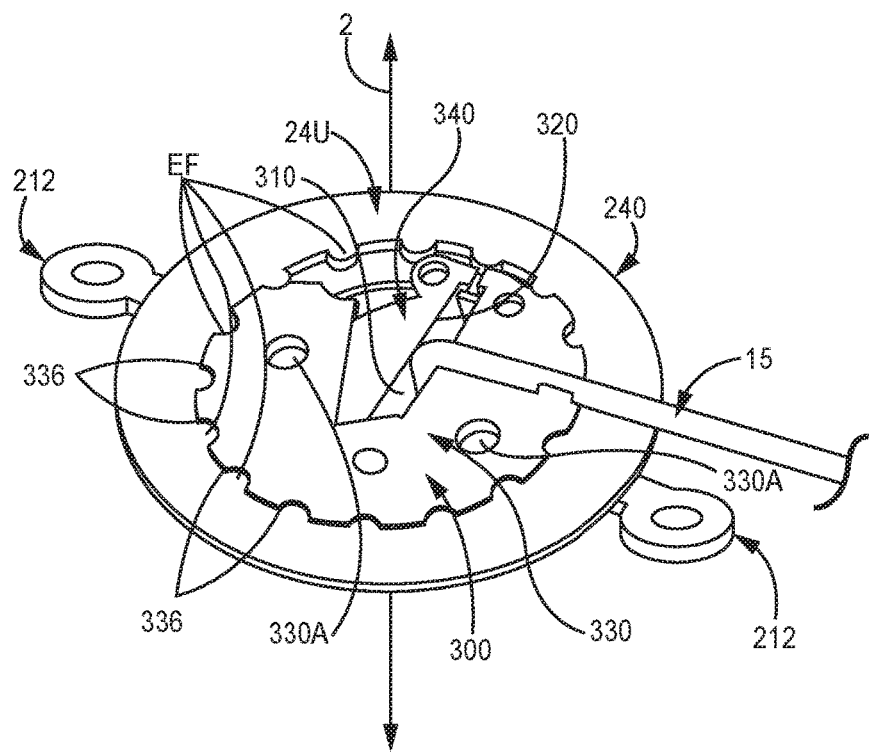
FIGS. 2E-F are perspective views of an anchoring mechanism attached to the apparatus of FIGS. 2A-D, according to some embodiments.
Figure 2F:
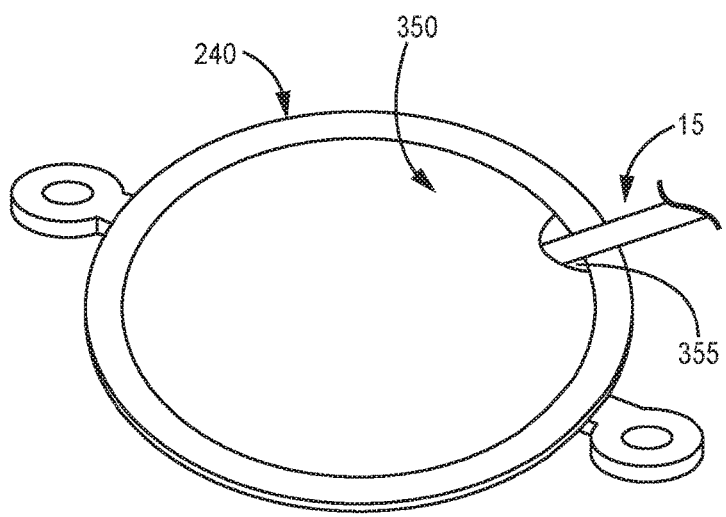

With further reference to FIG. 2A, an upper surface 24U of apparatus shell 240 defines a rim that has a plurality of uniform engagement features EF formed therein, which are equally spaced apart from one another around an entire perimeter of the rim. According to the illustrated embodiment, engagement features EF may be means to receive attachment of the aforementioned medical device anchoring mechanism that secures a portion of the implanted medical device in place, for example, elongate therapy delivery lead 15 (FIGS. 1A-C). Such an anchoring mechanism is described in co-pending and commonly assigned U.S. Provisional Patent Applications having Ser. Nos. 62/400,140 and 62/446,923, salient portions of which are hereby incorporated by reference. FIG. 2E is a perspective view of a clip or jaw 300 of such an anchoring mechanism seated against shell upper surface 24U of apparatus 200. FIG. 2E illustrates jaw 300 including a plurality of uniform interlocking features 336 formed in an outer perimeter edge of a first plate member 330 thereof, which interlock with engagement features EF of apparatus 200. FIG. 2E further illustrates first plate member 330 of jaw 300 including a sidewall 310 that has a gripping surface opposing that of a sidewall 320 of a second plate member 340 of jaw 300, wherein second plate member 340 is movable relative to first plate member 330 to open and close jaw 300. In FIG. 2E, jaw 300 is shown closed and gripping the implanted lead 15 between grip surfaces of sidewalls 310, 320. According to the illustrated embodiment, the uniformity of form and spacing of apparatus engagement features EF and jaw interlocking features 336 allow the operator to seat jaw 300 in a plurality of orientations about a longitudinal axis 2 of apparatus 200, for example, to accommodate a trajectory of the implanted lead 15 through burr hole 11. FIG. 2F is a perspective view of a cap 350 of the anchoring mechanism covering jaw 300 and including a channel 355 through which the anchored lead 15 passes. According to some embodiments, for example, like those described in the aforementioned co-pending and commonly assigned U.S. Provisional Patent Application Ser. Nos. 62/400,140 and 62/446,923, cap 350 includes studs that project from a lower surface thereof and are configured to mate in a press fit with apertures 330A (FIG. 2E) of jaw plate member 330.

Figure 3:
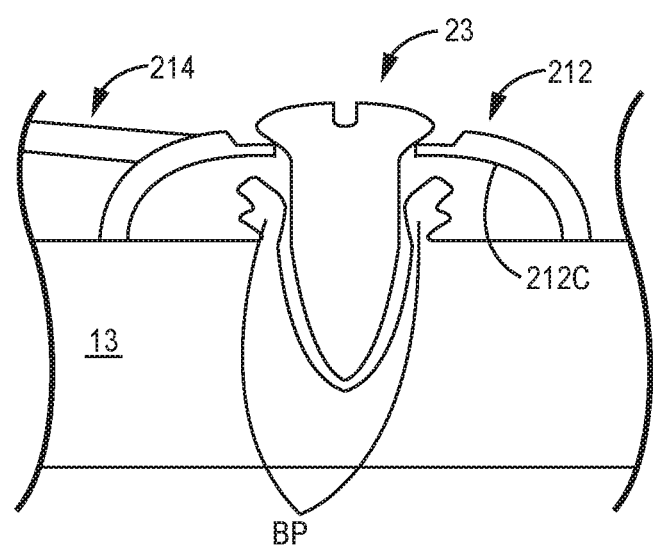
FIG. 3 is a schematic cross-section of a portion of the apparatus fastened to the patient's cranium, according to some embodiments.

With further reference to FIGS. 2B-C, each fastener member 212 of apparatus core 210 has an aperture to receive extension of a bone screw 23 therethrough for fastening apparatus 200 to the patient's cranium 13 when apparatus orifice 241 has been centered over cranial burr hole 11, for example, as described below in conjunction with FIGS. 4A-C. When each bone screw 23 is positioned through the corresponding fastener member 212 of the centered apparatus 200 and driven into cranium 13, for example as illustrated in the schematic cross-section of FIG. 3, each pliable arm 214 of core 210 may bend from the relaxed substantially flat form of core 210 to generally conform to the curvature of cranium 13. FIG. 3 further illustrates cranial bone material BP, which has been displaced by the driven bone screw 23, piled up in a pillar-like formation that surrounds screw 23. Because the displaced bone material BP is relatively hard and firm, and remains attached to cranium 13, unless some clearance between fastener member 212 and cranium 13 is provided, the fastened apparatus 200 may rock, or wiggle, and not provide a stable base for the aforementioned medical device anchoring mechanism. Thus, according to preferred embodiments, and with reference to FIGS. 2B and 3, each fastener member 212 of apparatus has a concave surface 212C facing in a same direction as lower surface 24L of shell 240 to provide clearance for displaced bone material BP. The aperture of each fastener member 212 is shown extending through an apex of the corresponding concave surface 212C. It should be noted that, according to some alternate embodiments, core 210 of apparatus 200 can include more than two pliable arms 214 and corresponding fastener members 212.

FIG. 4A is an elevation view of a placement tool 400 assembled together with apparatus 200, according to some system embodiments. FIG. 4A illustrates tool 400 including a central portion 440, which is aligned along a central axis 4 of tool 400, first and second arms 420, and first and second receptacles 430, each of which terminates a corresponding arm 420 and is configured to temporarily hold one of bone screws 23. According to an exemplary embodiment, tool 400 is formed from a relatively rigid medical grade plastic, such as polysulfone or PEEK, which may be molded into opposing mirror image parts that are subsequently snap fit together at seams 40. FIG. 4A further illustrates a lower part 44L of tool central portion 440 extending through orifice 241 of apparatus 200, and, a length of each tool arm 420, from an upper part 44U of central portion 440 to the corresponding receptacle 430, being such that each receptacle 430 is aligned over a corresponding fastener member 212 of apparatus. It should be noted that tool 400 can be configured with more than two arms 420 (and corresponding receptacles 430) to correspond to an apparatus 200 that has more than two arms 214 (and corresponding fastener members 212).

According to the illustrated embodiment, opposing elastically flexible legs 446 of tool central portion 440 can be pushed toward one another to insert central portion lower part 44L through apparatus orifice 241, and then released so that tool 400 holds apparatus 200 in a press fit. Central portion lower part 44L is configured to fit within cranial burr hole 11 so that tool 400 serves to center orifice 241 of the held apparatus 200 over burr hole 11, for example, as illustrated in FIGS. 4B-C. FIGS. 4B-C are a perspective view and a cross-section view of tool 400 fitted in cranial burr hole 11 to place apparatus 200 thereabout for fastening to cranium 13. FIGS. 4B-C illustrate each receptacle 430 of tool 400 extending from an upper opening 43U thereof to a lower opening 43L thereof, for example, along a longitudinal axis 3 thereof, so that each bone screw 23 can extend therethrough to be driven into cranium 13, through apertures of apparatus fastening members 212. With reference to FIG. 4B, tool 400 may be configured, for example, including one or more features 460, to help align receptacles 430 with apparatus fastener members 212 when inserting tool central portion 440 through apparatus orifice 241; and, according to some embodiments, features 460, which are shown located in proximity to an intersection of central portion upper part 44U and lower part 44L, are preferably configured to engage with apparatus upper surface 24U to prevent tool 400 from rotating relative to apparatus 200 as bone screws 23 are being driven through apertures of fastening members 212.

Figure 4C:
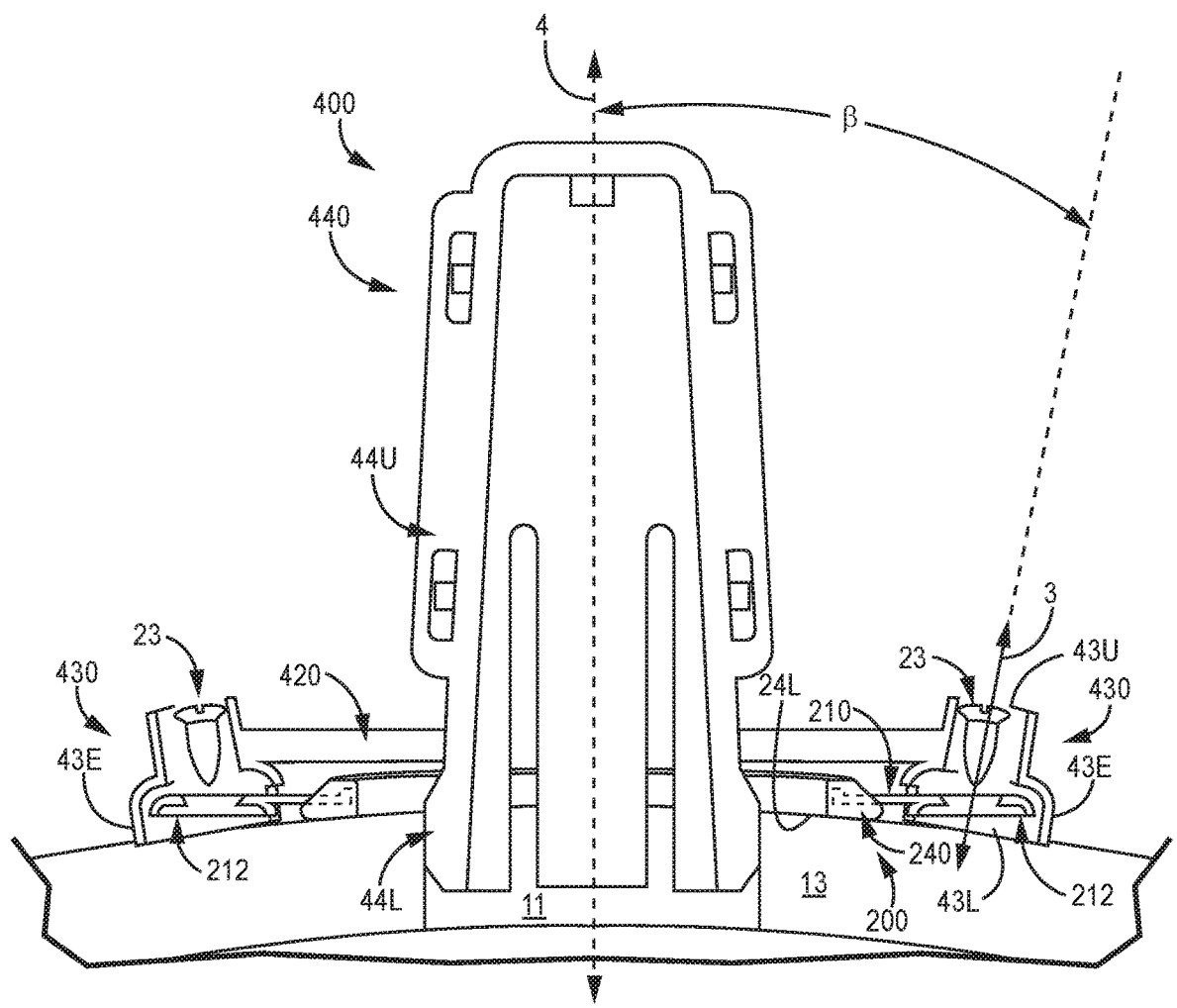

FIGS. 4A-C further illustrate each tool receptacle 430 including an extension 43E, according to some embodiments, wherein each extension 43E defines the corresponding receptacle lower opening 43L, being configured to shroud the corresponding fastener member 212 of the held apparatus 200. With reference to FIGS. 4A and 4C, although a lateral extension of first and second arms 420 from central portion upper part 44U is shown being substantially orthogonal to tool central axis 4, receptacle lower openings 43L are generally oriented along the curvature of the contour of lower surface 24L of apparatus shell 240, when tool 400 holds apparatus 200. Axes 3 of tool receptacles 430 are shown extending toward one another in a direction from upper opening 43U to lower opening 43L, and at an angle β with respect to tool central axis 4 resulting in the aforementioned orientation of receptacle lower openings 43L. As described above, apparatus arms 214 are pliable, so that when bone screws 23 are driven into cranium 13, arms 214 will bend to the curvature of cranium 13 along which lower surface 24L of apparatus shell 240 is shown extending.

In the foregoing detailed description, reference has been made to specific embodiments. However, it may be appreciated that various modifications and changes can be made without departing from the scope of the disclosure as set forth in the appended claims.

Furthermore various combinations of elements described above in conjunction with the specific embodiments, are within the scope of the present disclosure, for example, according to the following statements:

1. An apparatus configured to be fastened to a cranium, around a burr hole formed therethrough, and to receive attachment thereto a medical device anchoring mechanism, the apparatus comprising:
    a substantially flat core including a ring portion, first and second fastener members, and first and second pliable arms extending laterally from the ring portion, each arm being terminated by a corresponding fastener member of the first and second fastener members, and each fastener member having an aperture to receive extension of a bone screw therethrough;
    a shell encapsulating the ring portion of the core, the shell defining an orifice of the apparatus substantially centered within the ring portion of the core, and the shell including an upper surface and a lower surface, the lower surface having a contour to match the curvature of cranium around the burr hole.
2. The apparatus of statement 1, wherein each fastener member of the core comprises a concave surface that faces in a same direction as the lower surface of the shell, the aperture of each fastener member extending though an apex of the corresponding concave surface.

3. The apparatus of statement 1 or 2, wherein the core comprises a medical grade titanium and the shell comprises a medical grade polymer.

4. The apparatus of any of statements 1-3, wherein the upper surface of the shell defines a rim that has a plurality of uniform engagement features formed therein, the engagement features being equally spaced apart from one another around an entire perimeter of the rim, and the engagement features being means to receive attachment of the medical device anchoring mechanism.

5. A placement tool for the apparatus of any of statements 1-4, the placement tool comprising:
- a central portion including an upper part and a lower part generally aligned along a central axis of the tool, the lower part being configured to extend through the orifice of the apparatus and to fit within the burr hole;
- first and second receptacles, each receptacle being configured to hold a bone screw, each receptacle extending along a longitudinal axis thereof, from an upper opening thereof to a lower opening thereof, the longitudinal axes of the receptacles extending toward one another in a direction from the upper opening to the lower opening, and at an angle with respect to the central axis of the tool; and
- first and second arms, each arm extending laterally from the upper part of the central portion and being terminated by a corresponding receptacle of the first and second receptacles, a length of each arm from the central portion to the corresponding receptacle being such that the receptacle is generally aligned with the corresponding fastener member of the apparatus when the lower part of the central portion of the tool extends through the orifice of the apparatus.

6. The tool of statement 5, wherein the lateral extension of each arm is substantially orthogonal to the central axis.

7. The tool of statement 5 or 6, further comprising one or more features configured to engage with the upper surface of the apparatus shell, the one or more features being located in proximity to an intersection of the upper and lower parts of the center portion of the tool.

8. The tool of any of statements 5-7, wherein each receptacle includes an extension defining the lower opening thereof, the extension being configured to shroud the fastener member of the apparatus when the lower part of the central portion of the tool extends through the orifice of the apparatus.

9. A placement tool for the apparatus of any of statements 1-4, the placement tool comprising:
- a central portion including an upper part and a lower part, the lower part being configured to extend through the orifice of the apparatus and to fit within the burr hole;
- first and second receptacles, each receptacle being configured to hold a bone screw, each receptacle extending from an upper opening thereof to a lower opening thereof, the lower openings being generally oriented along the curvature of the contour of the lower surface of the apparatus shell, when the lower part of the central portion of the tool extends through the orifice of the apparatus; and
- first and second arms, each arm extending laterally from the upper part of the central portion and being terminated by a corresponding receptacle of the first and second receptacles, a length of each arm from the central portion to the corresponding receptacle being such that the receptacle is generally aligned with the corresponding fastener member of the apparatus, when the lower part of the central portion of the tool extends through the orifice of the apparatus.

10. The tool of statement 9, wherein the lateral extension of each arm is substantially orthogonal to the central axis.

11. The tool of statement 9 or 10, further comprising one or more features configured to engage with the upper surface of the apparatus shell, the one or more features being located in proximity to an intersection of the upper and lower parts of the central portion of the tool.

12. The tool of any of statements 9-11, wherein each receptacle includes an extension defining the lower opening thereof, the extension being configured to shroud the fastener member of the apparatus when the lower part of the central portion of the tool extends through the orifice of the apparatus.

13. A system including the apparatus of any of statements 1-4 and the tool of any of statements 5-12.

14. An implantable medical therapy system comprising a medical device, an anchoring mechanism for the device, and the apparatus of any of statements 1-4.

15. A kit comprising the system of statement 14 and the tool of any of statements 5-12.

The invention claimed is:

1. A system comprising:
a placement tool for use with an apparatus configured to be fastened to a cranium, around a burr hole formed therethrough, and to receive attachment thereto a medical device anchoring mechanism, the placement tool comprising:
- a central portion including an upper part and a lower part, the lower part being configured to extend through an orifice of the apparatus and to fit within the burr hole, wherein the central portion defines a central axis that extends between the upper part and the lower part and is substantially orthogonal to the orifice when the lower part extends through the orifice of the apparatus;
- first and second receptacles, each receptacle being configured to hold a bone screw, each receptacle extending from an upper opening thereof to a lower opening thereof, the lower openings being generally oriented along a contour of a lower surface of the apparatus when the lower part of the central portion of the tool extends through the orifice of the apparatus; and
- first and second arms, each arm extending laterally from the upper part of the central portion and being terminated by a corresponding receptacle of the first and second receptacles, a length of each arm from the central portion to the corresponding receptacle being such that the receptacle is generally aligned with a corresponding fastener member of the apparatus when the lower part of the central portion of the tool extends through the orifice of the apparatus;
- wherein each receptacle includes an extension defining the lower opening thereof, the extension being configured to shroud the fastener member of the apparatus as viewed in a plane parallel to the central axis when the lower part of the central portion of the tool extends through the orifice of the apparatus.

2. The system of claim 1, wherein each receptacle of the tool extends along a longitudinal axis thereof, from the upper opening thereof to the lower opening thereof, the longitudinal axes of the receptacles extending toward one another in a direction from the upper to the lower opening, and at an angle with respect to the central axis of the tool.

3. The system of claim 1, wherein the lateral extension of each arm of the tool is substantially orthogonal to the central axis of the tool.

4. The system of claim 1, wherein the system further comprises the apparatus.

5. The system of claim 4, wherein the apparatus further comprises:
   a substantially flat core including a ring portion, wherein the fastener member of the apparatus comprises first and second fastener members of the substantially flat core, and first and second pliable arms extending laterally from the ring portion, each arm being terminated by a corresponding fastener member of the first and second fastener members, and each fastener member having an aperture to receive extension of a bone screw therethrough; and
   a shell encapsulating the ring portion of the core, the shell defining an orifice of the apparatus substantially centered within the ring portion of the core, and the shell including an upper surface and a lower surface.

6. The system of claim 5, wherein the tool further comprises one or more features configured to engage with the upper surface of the apparatus shell, the one or more features being located in proximity to an intersection of the upper and lower parts of the central portion of the tool.

7. The system of claim 6, further comprising an anchoring mechanism, wherein the anchoring mechanism comprises a jaw seated against the upper surface of the shell.

8. The system of claim 7, wherein the jaw comprises a first plate member and a second plate member, wherein each of the first and second plate members comprises a sidewall and a gripping surface, wherein the gripping surface of the first plate member is opposed to the gripping surface of the second plate member.

9. The system of claim 8, wherein the jaw further comprises a plurality of uniform interlocking features formed in an outer perimeter edge of the first plate member, wherein the plurality of uniform interlocking features interlock with engagement features formed in a rim defined by the upper surface of the shell of the apparatus.

10. The system of claim 8, wherein the second plate member is movable relative to the first plate member to open and close the jaw.

11. The system of claim 7, wherein the anchoring mechanism further comprises a cap that is adapted to cover the jaw.

12. The system of claim 11, wherein the cap comprises a channel through which an anchored lead passes.

13. The system of claim 11, wherein the cap comprises one or more studs that project from a lower surface of the cap, wherein the one or more studs are configured to mate in a press fit with one or more apertures of the first plate member of the jaw.

14. A placement tool for an apparatus, the apparatus being configured to be fastened to a cranium, around a burr hole formed therethrough, and to receive attachment thereto a medical device anchoring mechanism, the placement tool comprising:
   a central portion including an upper part and a lower part, the lower part being configured to extend through an orifice of the apparatus and to fit within the burr hole, wherein the central portion defines a central axis that extends between the upper part and the lower part and is substantially orthogonal to the orifice when the lower part extends through the orifice of the apparatus;
   first and second receptacles, each receptacle being configured to hold a bone screw, each receptacle extending from an upper opening thereof to a lower opening thereof, the lower openings being generally oriented along a curvature of a contour of a lower surface of the apparatus when the lower part of the central portion of the tool extends through the orifice of the apparatus; and
   first and second arms, each arm extending laterally from the upper part of the central portion and being terminated by a corresponding receptacle of the first and second receptacles, a length of each arm from the central portion to the corresponding receptacle being such that the receptacle is generally aligned with a corresponding fastener member of the apparatus when the lower part of the central portion of the tool extends through the orifice of the apparatus;
   wherein each receptacle includes an extension defining the lower opening thereof, the extension being configured to shroud the fastener member of the apparatus as viewed in a plane parallel to the central axis when the lower part of the central portion of the tool extends through the orifice of the apparatus.

15. The tool of claim 14, wherein each receptacle extends along a longitudinal axis thereof, from the upper opening thereof to the lower opening thereof, the longitudinal axes of the receptacles extending toward one another in a direction from the upper to the lower opening, and at an angle with respect to the central axis of the tool.

16. The tool of claim 14, further comprising one or more features configured to engage with an upper surface of the apparatus, the one or more features being located in proximity to an intersection of the upper and lower parts of the central portion of the tool.

17. An implantable medical therapy system comprising:
   an implantable medical device;
   an elongate therapy delivery device configured to couple to the implantable medical device;
   an anchoring mechanism configured to anchor the therapy delivery device;
   an apparatus configured to be fastened to a cranium around a burr hole formed therethrough, and to receive attachment thereto a medical device anchoring mechanism; and
   a placement tool for the apparatus, the tool comprising:
      a central portion including an upper part and a lower part, the lower part being configured to extend through an orifice of the apparatus and to fit within the burr hole, wherein the central portion defines a central axis that extends between the upper part and the lower part and is substantially orthogonal to the orifice when the lower part extends through the orifice of the apparatus;
      first and second receptacles, each receptacle being configured to hold a bone screw, each receptacle extending from an upper opening thereof to a lower opening thereof, the lower openings being generally oriented along a contour of a lower surface of the apparatus when the lower part of the central portion of the tool extends through the orifice of the apparatus; and
      first and second arms, each arm extending laterally from the upper part of the central portion and being terminated by a corresponding receptacle of the first and second receptacles, a length of each arm from the central portion to the corresponding receptacle being such that the receptacle is generally aligned with an aperture of a corresponding fastener member of the apparatus when the lower part of the central portion of the tool extends through the orifice of the apparatus;

wherein each receptacle of the tool includes an extension defining the lower opening thereof, the extension being configured to shroud the fastener member of the apparatus as viewed in a plane parallel to the central axis when the lower part of the central portion of the tool extends through the orifice of the apparatus.

18. The system of claim 17, wherein each receptacle of the tool extends along a longitudinal axis thereof, from the upper opening thereof to the lower opening thereof, the longitudinal axes of the receptacles extending toward one another in a direction from the upper to the lower opening, and at an angle with respect to the central axis of the tool.

19. The system of claim 17, wherein the lateral extension of each arm of the tool is substantially orthogonal to the central axis of the tool.

20. The system of claim 17, wherein the tool further comprises one or more features configured to engage with an upper surface of a shell of the apparatus, wherein the shell defines the orifice of the apparatus, wherein the one or more features are located in proximity to an intersection of the upper and lower parts of the central portion of the tool.

* * * * *